(12) United States Patent
Webler

(10) Patent No.: US 7,041,097 B1
(45) Date of Patent: May 9, 2006

(54) SYSTEM AND METHOD FOR ACCESSING THE CORONARY SINUS

(75) Inventor: William E. Webler, Escondido, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/748,405

(22) Filed: Dec. 21, 2000

(51) Int. Cl.
*A61B 17/39* (2006.01)
*A61B 18/04* (2006.01)
*A61M 25/00* (2006.01)

(52) U.S. Cl. .......................... 606/41; 606/33; 600/434
(58) Field of Classification Search ................ 604/528, 604/523, 158, 22, 95.01, 263, 525, 532, 6.01, 604/96.01, 921; 606/108, 15, 41, 47, 49, 606/192, 33; 600/434, 585, 374, 375, 393
See application file for complete search history.

(56) References Cited

U.S. PATENT DOCUMENTS

| | | | | |
|---|---|---|---|---|
| 4,033,331 A | * | 7/1977 | Guss et al. | ................ 600/434 |
| 4,969,890 A | * | 11/1990 | Sugita et al. | ................ 606/192 |
| 5,423,772 A | | 6/1995 | Lurie et al. | |
| 5,488,960 A | | 2/1996 | Toner | |
| 5,775,327 A | | 7/1998 | Randolph et al. | |
| 5,882,333 A | | 3/1999 | Schaer et al. | |
| 5,902,268 A | * | 5/1999 | Saab | ................ 604/96.01 |
| 6,021,340 A | | 2/2000 | Randolph et al. | |
| 6,120,500 A | * | 9/2000 | Bednarek et al. | ............. 606/41 |
| 6,251,104 B1 | | 6/2001 | Kesten et al. | |
| 6,277,107 B1 | | 8/2001 | Lurie et al. | |
| 6,332,881 B1 | * | 12/2001 | Carner et al. | ................ 606/41 |

* cited by examiner

Primary Examiner—Nicholas D. Lucchesi
Assistant Examiner—Roz Maiorino
(74) Attorney, Agent, or Firm—Hollingsworth & Funk, LLC (57) ABSTRACT

The invention is generally directed to an accessing system for a patient's coronary sinus which includes a tubular support member with a distal extremity extending into the right atrium of the patient's heart. A guide member is disposed within a first lumen of the tubular support member and advanced out an angled distal tip, through the patient's coronary sinus ostium and into the coronary sinus. A stabilizing member, similar to a conventional intravascular guidewire, is disposed within a second lumen of the tubular support member and extends into the right ventricle of the patient and is seated in the apex thereof. To advance the guide member into the CS ostium, the position of the distal extremity of the tubular support member is adjusted within the atrial chamber by moving longitudinally along or rotating about (or both) the stabilizing member and the guide member is advanced into the CS ostium. These steps may be repeated in a predetermined pattern in order to pass into the coronary sinus ostium.

45 Claims, 7 Drawing Sheets

SYSTEM AND METHOD FOR ACCESSING THE CORONARY SINUS

FIELD OF INVENTION

The invention relates to the field of intravascular catheters, and particularly to a catheter suitable for accessing a patient's coronary sinus to facilitate delivery of therapeutic and diagnostic devices and agents.

BACKGROUND OF THE INVENTION

Congestive heart failure (CHF) is a condition in which the heart is unable to pump enough blood to meet the metabolic needs of a patient's body. The condition results in the patient having shortness of breath, weakness and a lack of stamina, fatigue, exercise intolerance and fluid retention which results from an inadequate flow of blood to the patient's kidneys. CHF is a progressive disease that involves the continuing enlargement of the heart muscle in response to the low blood output (cardiac output). The harder the heart works to pump more blood, the more enlarged it becomes. The more enlarged the heart becomes, the more work the heart must do to pump the same amount of blood. The progressive cycle of the disease has few symptoms until the heart is unable to do more work. Often, by the time symptoms are noticed by the patient, the enlargement is pronounced and the heart is unable to provide enough cardiac output to support normal lifestyle activity. Drug treatments that attempt to increase cardiac output tend to facilitate the progression of the disease. Conversely, drug treatments that lower cardiac output tend to slow the progression of the disease. However, this can severely limit the patients lifestyle, leaving many patients effectively immobile or worse. Many CHF patients require extensive and expensive treatments both on an in-patient and out-patient basis.

CHF affects well over three million people in the United states alone. Moreover, there are over 400,000 new cases of CHF diagnosed every year.

The enlarged hearts of many CHF patients do not contract in the normal manner in that the right and left ventricles of the heart do not contract at the same time. This lack of synchronicity causes the heart to pump less blood than it would if they were to contract together. Conventional pacing of the right ventricle (RV) or right atrium (RA) has not been found to be effective in causing the left ventricle (LV) to contract at the same time as the RV in most CHF patients. In many CHF patients, the natural conductance of the heart between the RA, RV and the LV has been compromised.

Others have attempted to treat CHF by placing pacing leads in the right heart (RA and/or RV) and on the outside of the LV. These pacing leads are connected to a power source that supplies electrical signals to the right heart and to the LV to cause them to contract in the normal manner. This has been found to be effective in controlling cardiac contractions. However, placing the pacing lead on the outside of the LV requires a surgical procedure which is both expensive and risky, especially given the weakened condition of CHF patients.

The present assignee, Guidant Corporation, has recently introduced a treatment for CHF wherein a pacer lead for the LV is advanced through the ostium or opening of the coronary sinus (located in the RA) and into the venous drainage system of the LV which drains into the coronary sinus. This allows the RA and/or RV and LV pacer lead placement for CHF treatment utilizing the less invasive and less risky percutaneous catheterization procedures used to position the RA and/or RV lead(s) in conventional pacing. Thus many more CHF patients with conduction abnormalities can be treated. This procedure has been found to greatly enhance the heart's pumping efficiency and to increase the patient's cardiac output to the extent that the patient can frequently resume normal daily activity and/or benefit from drug therapy.

To access the coronary sinus through the ostium thereof, typically a guiding catheter with a shaped distal extremity is introduced into a vein in the patient's chest using a percutaneous catheterization procedure. The guiding catheter is advanced through the patient's vasculature until its distal end is within the patient's RA via the superior vena cava. Approaches via the superior vena cava are preferred over via the inferior vena cava for two reasons. The chest area is used for implanting the power source and is, therefore, already prepped and easily accessible. The inferior vena cava approach involves cannulating the femoral vein, which is more prone to infection and requires longer and, therefore, more difficult to control devices. To seat the distal end of the guiding catheter in the coronary sinus ostium, the proximal end of the guiding catheter which extends outside of the patient is torqued to rotate the shaped distal end while further advancing the catheter so as to guide the distal tip of the guiding catheter into the ostium of the patient's coronary sinus.

The ostium of the coronary sinus, which drains the venous blood from the heart muscle into the RA, is in varying positions, guarded by valve-like flaps of varying shape and resides in an RA of varying shape. The ostium is generally located between the tricuspid valve and the inferior vena cava, near the inferior base of the RA. Additionally, the path of the coronary sinus just distal to its ostium may take off from the ostium in various curves or angles. These variations are especially pronounced from CHF patient to CHF patient. Therefore, much time can be consumed attempting to place the distal tip of the guiding catheter into the ostium and to advance the distal tip an appropriate distance within the coronary sinus.

Once placed within the coronary sinus, the distal tip of the guiding catheter can be easily dislodged during the subsequent advancement of a guidewire into position within the vasculature of the coronary sinus which is employed to deliver the pacing lead into the coronary sinus. The tip may be easily dislodged, because it is unlikely that the shape of the distal portion of the guiding catheter will match the shape of the RA closely enough to provide good support (resist guiding catheter tip movement). Also the orientation of the distal tip of the guiding catheter may not match the take off curve or angle of the coronary sinus, causing any inserted devices to immediately contact the wall of the coronary sinus. Thus, as a guidewire is manipulated and advanced through the guiding catheter into the coronary sinus, the force that the guidewire applies to the wall of the guiding catheter may push the distal tip of the guiding catheters out of the ostium. This may result in a damaged guidewire and/or loss of access to the coronary sinus.

Once the guidewire is positioned well within the coronary sinus, the current procedure is to replace the guiding catheter with a special lead placement catheter. If, due to lack of guide support or the proper orientation of its tip, the guidewire is not deep enough into the coronary sinus, then the guiding catheter may pull the guidewire out of the coronary sinus as the guiding catheter is removed during the replacement procedure.

The coronary sinus, which drains the venous side of the patient's heart into the right atrium through the ostium, is at a difficult position, so much time can be taken merely to place the distal tip of the catheter within the ostium. Passing a pacing lead through the lumen of the guiding catheter can displace the guiding catheter, requiring the replacement thereof into the coronary sinus ostium.

It has been found that the procedure of accessing the coronary sinus of a patient's heart having CHF, is very time consuming. The hearts of CHF patients are deformed, so that finding the coronary sinus ostium is difficult. The existing guiding catheters used for other purposes have been found to be very ineffective in both finding the coronary sinus ostium and once found, maintaining access with the coronary sinus during the procedure.

The present invention satisfies these and other needs.

SUMMARY OF THE INVENTION

The invention is generally directed to an accessing system for a patient's intracorporeal opening of a body cavity such as the coronary sinus ostium and particularly for advancing therapeutic and diagnostic devices into the patients coronary sinus and related cardiac veins. The improved accessing system facilitates location of the patient's coronary sinus ostium, the advancement of therapeutic or diagnostic devices into the coronary sinus and associated coronary veins and maintaining the position of such devices during the procedure, particularly with patients having deformed hearts such as those suffering from CHF.

The accessing system of the invention includes a tubular support member which is configured to have a shaped distal end which extends into the patient's right atrium and which has a first inner lumen in fluid communication with a port in the shaped distal end. The shaped distal end of the tubular support member is at an angle in the range of about 30° to about 120° with respect to the longitudinal axis of the tubular support member.

In an alternate embodiment, the tubular support member may include a tendon or tendons and perhaps a shaping member in conjunction with a suitable tendon control device to allow the physician to adjust the angle of its shaped distal end.

A guide member is disposed within the first inner lumen of the tubular support member for longitudinal movement within the inner lumen and out the distal end of the tubular support member. The distal end of the guide member may include a bend or shape to facilitate its passage into the proximal portion of the coronary sinus in CHF hearts and to aid in orienting devices inserted through or over it away from the wall of the coronary sinus. In one presently preferred embodiment the distal end of the guide member has a 10° to 50° bend.

In this manner, the distal end of the tubular support member directs the guide member, as it extends, toward the RA wall. One or more stabilizing members are associated with the tubular support member to stabilize the position of the tubular support member's distal end relative to the patient's right atrium and, therefore, relative to the patient's coronary sinus ostium. This stabilization provides the support necessary for inserting the guide member and, subsequently, other devices via the guide member into the coronary sinus. Also the stabilizing member(s) create a stable repeatable path about which the tubular support member may be rotated and/or translated longitudinally along within the patient's right atrium. By rotating and longitudinally moving the tubular support member and longitudinally moving the guide member within it, the contact locations on the atrium wall by the distal end of the guide member can sweep over a wide region. A pattern of sequential sweeps or contact locations of the distal end of the guide member against the atrial wall ensures rapid accessing of the ostium of the patient's coronary sinus. Rotation and/or longitudinal movement of the tubular support member will point the shaped distal end of the tubular support member so that the distal end of the guide member will make a series of contacts with or sweeps against the atrial wall in a series of vertical, horizontal or other patterned contact locations. As physicians gain experience with this device, they will quickly settle on their preferred search pattern/technique to most quickly locate and gain access to the coronary sinus.

Because the superior vena cava approach is preferred, as explained previously, the embodiments described herein will be directed to that approach. However, the concepts and devices of this invention can be easily adapted to the inferior vena cava approach by one skilled in the art.

In one presently preferred embodiment of the invention, the stabilizing member is a guidewire-like elongated device which has a non-traumatic distal end, e.g. J-shaped, configured to rest in the apex of the patient's right ventricle. In this embodiment the stabilizer may be slidably disposed within a second lumen which extends within the tubular support member to a second opening in the distal extremity of the tubular support member. It is preferred that the guidewire-like elongated device contain a stiffened section that is just proximal to the non-traumatic tip and extends proximally, at least, an appropriate distance into the superior vena cava. Thus, this stiffened section would be supported on its distal end by the non-traumatic tip's contact with the apex of the right ventricle and supported on its proximal end by its contact with the wall of the superior vena cava as it curves away from the right atrium. Thus, the position of the shaped distal end of the tubular support member within the right atrium will be stabilized by the engagement of the tubular support member with the stabilized or stiffened section of the guidewire-like elongated device. In some designs, it may also be advantageous to stiffen a proximal portion of the guidewire-like elongated device to facilitate the manipulation of the tubular support member. The materials and techniques of grinding, coiling, joining and other processes involved in designing and making a suitable the guidewire-like elongated device are well known to those skilled in the art of guidewire design and development and may follow conventional techniques.

In this embodiment, it is also preferred that a clamp device be used to fix the proximal end of the guidewire-like elongated device relative to the patient or the proximal end of the introducer sheath. This ensures that the non-traumatic tip of the guidewire-like elongated device remains positioned in the apex of the right ventricle and is not subject to much rotation or translation during manipulations of the tubular support and guide members. This provides further stabilization. If the guidewire-like elongated device were designed such that its non-traumatic tip can rotate or the rotation of the non-traumatic tip will not damage the RV or the guidewire-like elongate device, then the clamp device may allow rotation of the guidewire-like elongated device. The clamp device may also serve as a stable platform for the manipulation (rotation and translation) of the tubular support member about the proximal end of the guidewire-like elongated device.

In another embodiment of the invention, the stabilizing member is a guiding catheter having a shaped distal end which is configured to hold the tubular support member in a desired orientation within the patient's right atrium while trying to locate the CS ostium and delivering the guide member into the patient's CS and advancing the guide member into related blood vessels which drain into the CS. The shaped distal end of the guide catheter should be relatively stiff in order to hold its position in the RA and thus provide a stabilized platform from which to manipulate the tubular support member.

In this embodiment, it is preferred that the distal end of the tubular support member incorporate a spring-like wire or other material construction to provide an elastically deformable, but stiffened section. This section would be proximal of the tubular support member's shaped end and extend proximally into the distal end of the guiding catheter during use. This section would increase the ability for the guiding catheter to support the tubular support member during use and ensure the path repeatability of tubular support member as it is advanced, retracted or rotated within the guiding catheter. As before, it is also preferred that a clamp device be provided that fixes the position of the proximal end of the guiding catheter relative to the patient or the proximal end of the introducer sheath to provide additional stabilization.

Other devices may be employed as stabilizing members. For example, the tubular support member itself may be provided with a plurality of arms which swing outwardly to contact the walls of the right atrium and thereby stabilize the tubular support member. Similar arms may be provided on the distal end of a guiding catheter such as that described in one of the previous embodiments which are designed to extend outwardly when reaching the interior of the right atrium to engage the walls of the atrium and thereby stabilize the tubular support member. A wide variety of other means may be employed to stabilize the tubular support member.

Once the guide member is disposed within the CS or one of the blood vessels which drain into the CS, a therapeutic or diagnostic device can be advanced through the guide member, if it is a tubular device, or over the guide member if it is a guidewire-like or similar device. In the presently preferred procedure for treating patient's having CHF, the therapeutic device is a pacing lead which is advanced deep into the Great Cardiac Vein in order to pace the left ventricle.

The guide member may be to stiff or have dimensions which preclude its advancement through the coronary sinus or deep enough into the patient's cardiac veins which drain into the coronary sinus. In this case a second guiding member having the requisite flexibility and/or dimensions may be advanced through or over the first guide member into the CS or veins draining into the CS.

The present invention provides a convenient user-friendly system for rapid location of a patient's CS ostium and advancement of a therapeutic or diagnostic device within the patient's CS and the blood vessels which drain into the CS. These and other advantages of the invention will become more apparent from the following detailed description of the invention and the accompanying exemplary drawings.

DETAILED DESCRIPTION OF THE INVENTION

FIGS. 1 through 4 illustrate a tubular support member 10 embodying features of the invention which generally includes an elongated shaft 11 with a proximal shaft section 12, a distal shaft section 13 and a distal tip 14 which curves away from the longitudinal axis 15 an angle θ. The angle may vary depending upon the desired attack angle to the coronary sinus opening but generally will be from about 20° to about 70°, preferably about 30° to about 60°. The distal tip 14 may be preshaped with the prescribed angular orientation with respect to the longitudinal axis 15 or the tubular support member 10 may be provided with one or more control strands or wires (not shown) within the wall thereof which may be manipulated from the proximal end of the tubular member 10 to configure the distal tip to the desired shape after distal tip is disposed within the patient's right atrium.

Figures 1, 2:
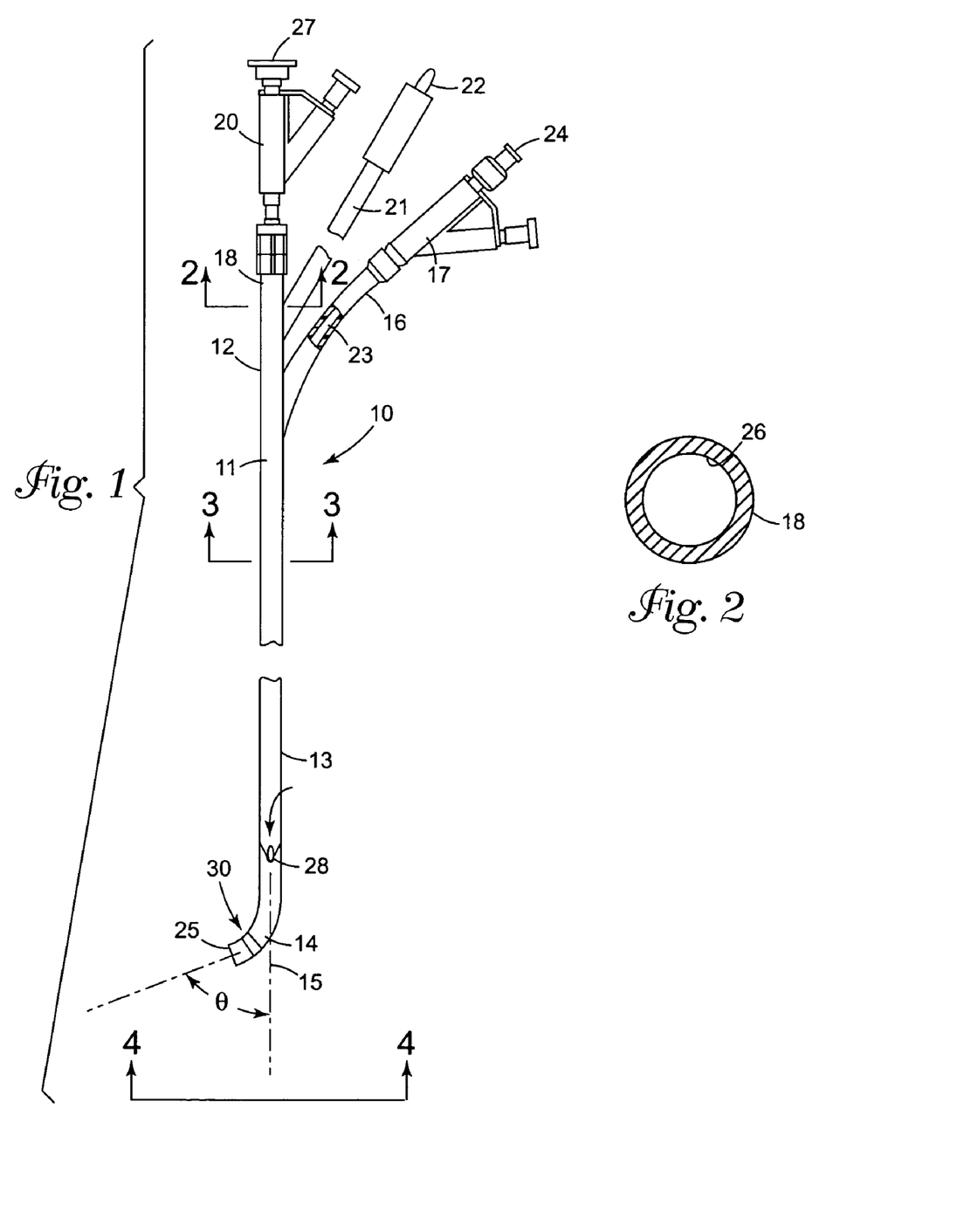
FIG. 1 is a schematic, elevational view of a tubular support member which embodies features of the invention.
FIG. 2 is a transverse cross sectional view of the tubular support member shown in FIG. 1 taken along lines 2—2.
Figure 3:
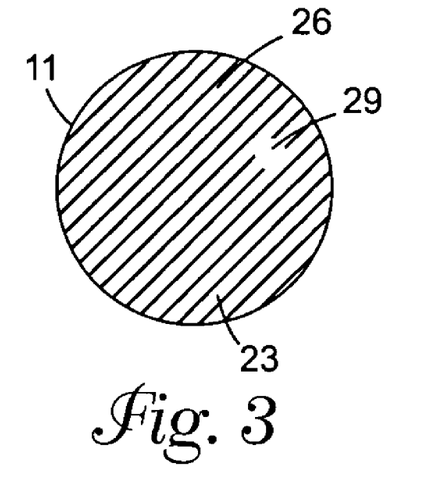
FIG. 3 is a transverse cross sectional view of the tubular support member shown in FIG. 1 taken along lines 3—3.
Figure 4:
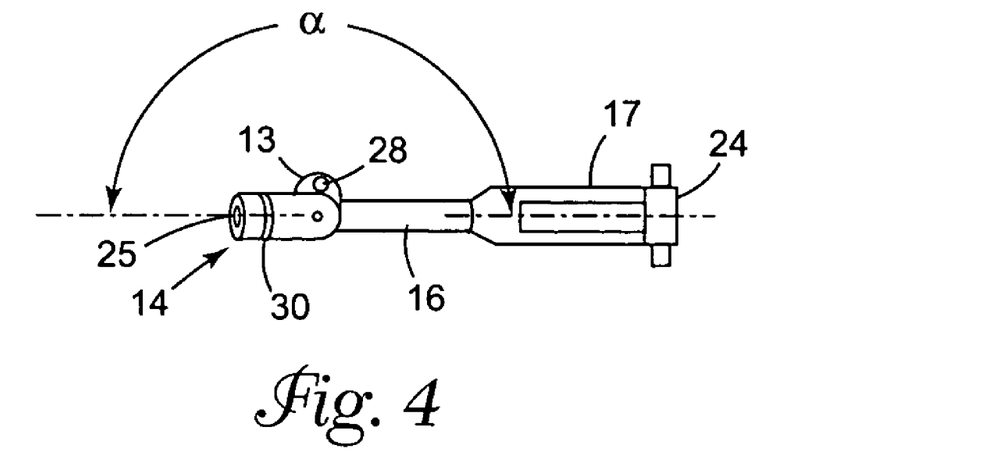
FIG. 4 is an end view of the tubular support member shown in FIG. 1 taken along the lines 4—4.

The proximal shaft section 12 includes a first proximal extension 16 which has an adapter 17 on the proximal end of the extension. The proximal shaft section 12 also includes a second proximal extension 18 having an adapter 20 on the proximal end thereof. The proximal shaft section 12 has a third proximal extension 21 with an electrical connector or jack 22 at the proximal end thereof which is configured to be connected to signal receiver and display device (not shown).

The tubular support member 10 has a first inner lumen 23 which extends between the port 24 in adapter 17 through the first proximal extension 16, the shaft 11 and the curved distal tip 14 and is in fluid communication with the port 25 provided in the distal tip 14. A second lumen 26 extends from the port 27 in adapter 20 through the second proximal extension 18 and the shaft 11 and is fluid communication with port 28 in the shaft 11 proximal to the distal tip 14. An electrical conductor 29 extends through third proximal extension 21, the wall of the shaft 11 and is electrically connected to the electrode 30 on the curved distal tip 14 which allows the physician to detect signals from the patient's heart which helps the physician in finding the CS ostium. The pulse signal from electrode 30 is usually compared with the pulse signal from separate reference electrode (not shown) on the exterior of the patient's body such as the patient's left leg or on the patient's chest.

Figures 5, 6, 7, 8:
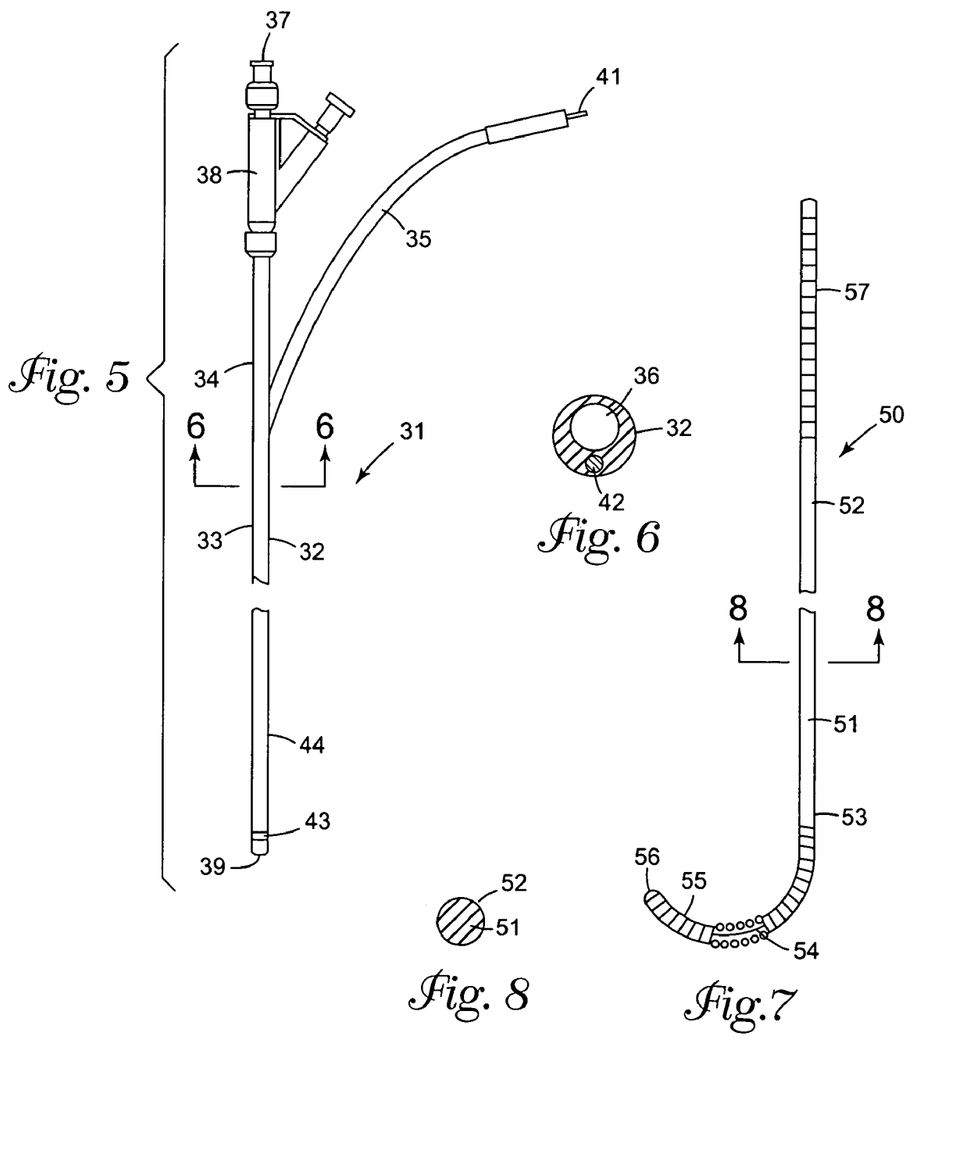
FIG. 5 is an elevational view of a guide member which embodies features of the invention.
FIG. 6 is a transverse cross-sectional view of the guide member shown in FIG. 5 taken along the lines 6—6.
FIG. 7 is an elevational view of a stabilizing member which embodies features of the invention.
FIG. 8 is a transverse cross sectional view of the stabilizing member shown in FIG. 7 taken along lines 8—8.

The guide member 31, which is depicted in FIGS. 5 and 6, generally has an elongated shaft 32, longer than the tubular support member 10, which includes a proximal shaft section 33 with a first proximal extension 34 and a second proximal extension 35. As shown in FIG. 6 guide member 31 has an inner lumen 36 which extends through the length of the guide member 31 from port 37 in the proximal end of the adapter 38 on the first proximal extension 33 to the port 39 provided in the distal end of guide member 31. The adapter 38 has a side arm 40 for flushing fluid and the like through the inner lumen 36 and out the port 39 in the distal end of the member 31. The exterior of shaft 32 is configured to be slidably disposed within the first inner lumen 23 in shaft 11 of the tubular support member 10. The inner lumen 36 of the guide member 31, as best shown in FIG. 6, is configured to slidably receive a therapeutic or diagnostic device through the port 37 which will extend out the distal port 39 into a patient's CS or blood vessel such as the Great Cardiac Vein or other blood vessel which drains into the patient's CS. The second proximal extension 35 has an electrical connector or jack 41 on its proximal end which is configured for connection to a signal receiver and display unit (not shown) which may be the same unit used for connection to the electrical jack 22 on the tubular support member 10. An electrical conductor 42 extends longitudinally through the wall of the elongated shaft 32 and is electrically connected by its proximal end to the electrical connector 41 and by its distal end to the electrode 43 provided on the distal section 43 of the shaft 32. The shaft 32 is sufficiently longer than the tubular support member 10 so as to extend out the port 25 in the distal tip 14 of the tubular support member 10 a desire length so as to be seated within the patient's coronary sinus opening and extend into the patient's CS a desired distance.

FIGS. 7 and 8 depict a stabilizing member 50 which is also longer than the tubular support member 10 and which has an elongated core member 51, similar in many respects to the core members found in commercially available guidewires. The elongated core member 51 has a proximal shaft section 52 with a uniform diameter over a substantial length thereof which is relatively stiff and a distal shaft section 53 which has one or more portions (not shown) which distally taper to smaller transverse dimensions so as to provide increased flexibility over the proximal shaft section 52. A flexible coil 55 is disposed about and secured to the distal end of the core member 51 by welding, soldering, brazing and the like to form a smooth round distal tip or plug 56. The proximal section 52 may be provided with a plurality of indicia 57 to facilitate raising/lowering the tubular support member 10 within the patient's right atrium a desired amount. The core member 51 is preferably solid as shown in the transverse cross-sectional view of FIG. 7. However, a hollow tube such as that made from hypotubing of suitable material or a hypotube filled with other material (e.g. radiopaque material) may be utilized as the core member. Suitable material for the core, whether solid or hollow, includes stainless steel, superelastic NiTi alloys with a stable austenite phase at or below body temperature and exhibiting stress induced transformation to martensite and high strength Co—Cr alloys such as MP35N, Elgiloy and L605. The high strength alloys are preferably precipitation hardened to improve properties.

Figures 9, 10:
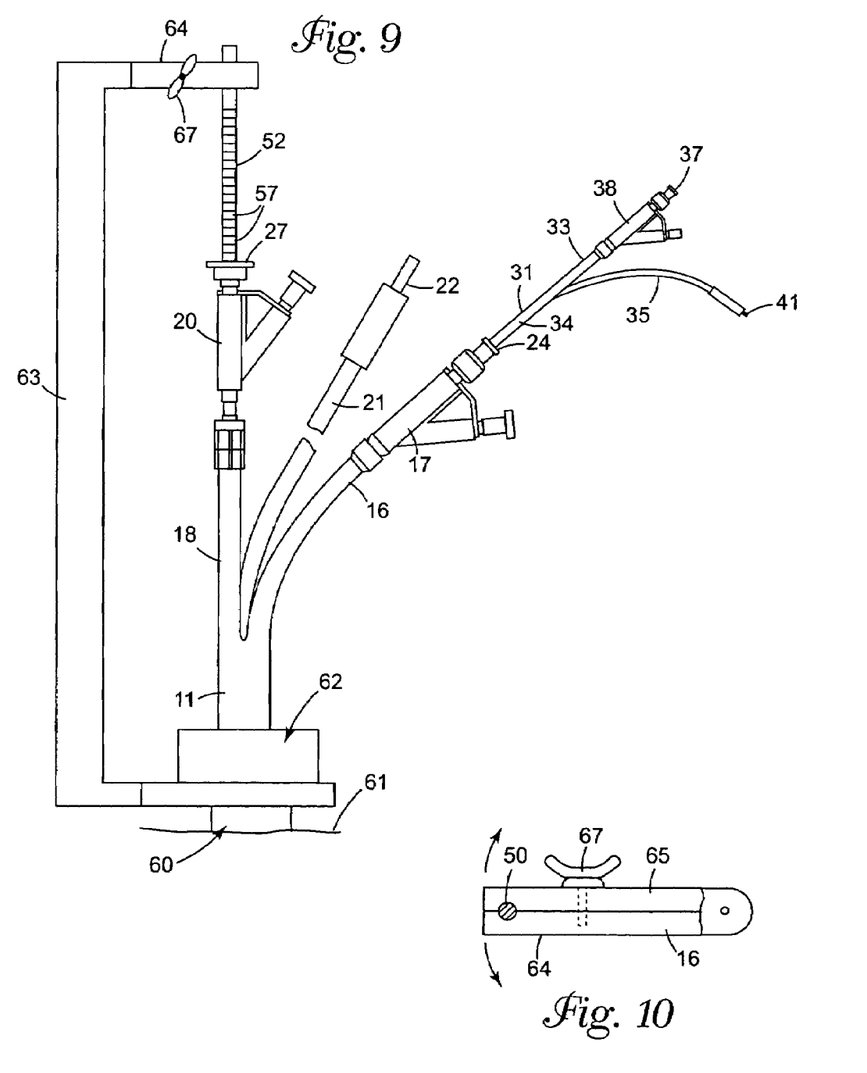
FIG. 9 is a partial elevational view of the proximal extremity of an assembled coronary sinus accessing system disposed with the proximal extremity shown extending out the proximal end of an introducer which extends out of the patient.
FIG. 10 is a top view of a clamp engaging the proximal extremity of the stabilizing member of the accessing system shown in FIG. 8.
Figure 11:
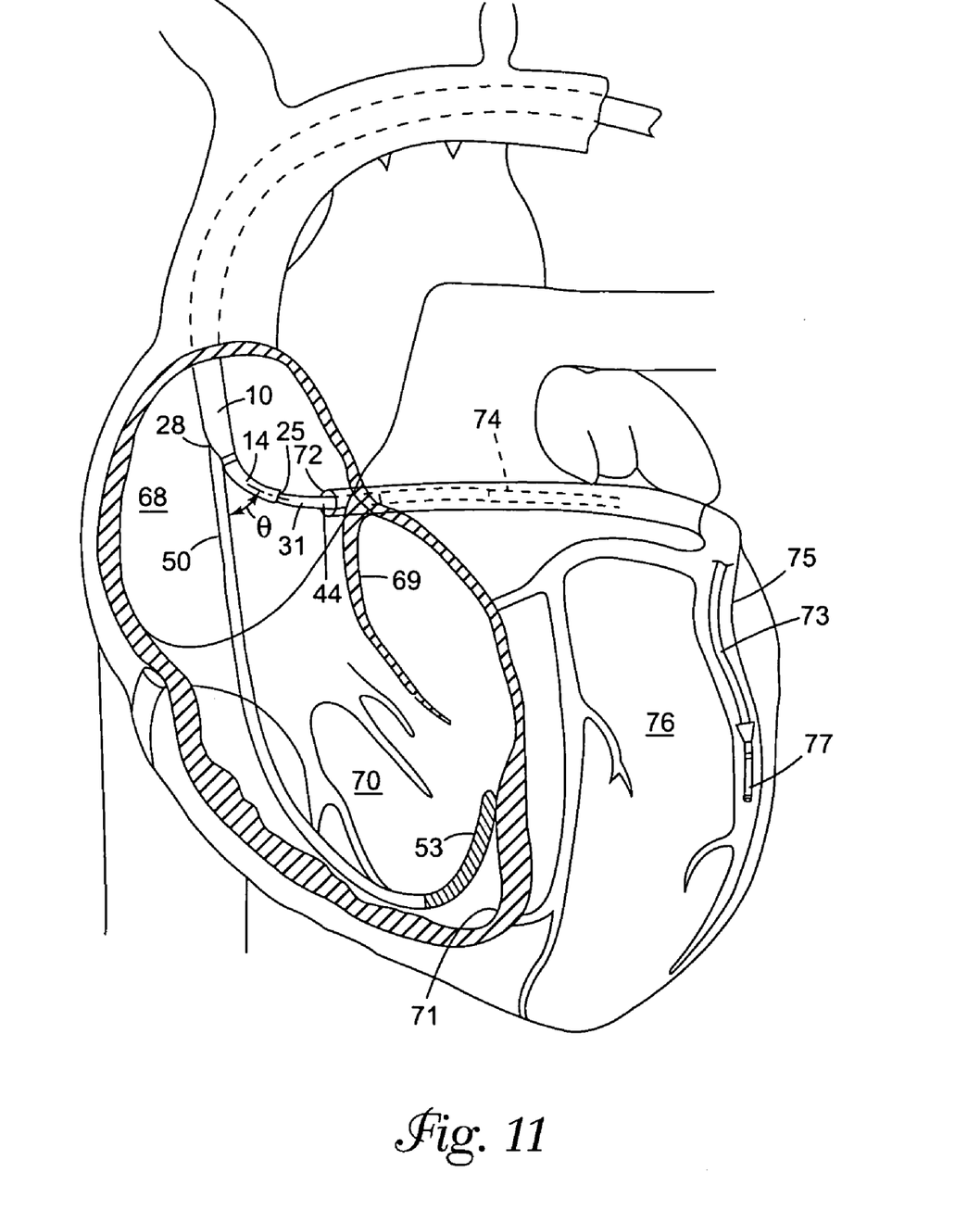
FIG. 11 is schematic elevational view of the distal portion of the accessing system shown in FIG. 6 operationally disposed within the patient's right atrium and right ventricle with a pacing lead disposed within a cardiac vein adjacent the left ventricle.

FIGS. 9–11 illustrate the disposition of the CS accessing system shown in FIGS. 1–8 which embodies features of the invention within a patient. FIG. 9 depicts the proximal shaft section 12 of the tubular support member 10, the proximal section of guide member 31 with proximal extensions 34 extending out of the proximal end of an introducer 60 which is disposed within a desired blood vessel (not shown) of the patient 61. A hemostasis valve 62 may be provided on the proximal end of the introducer 60 to prevent back bleed from the blood vessel in which the introducer is deployed. Hemostasis valves may also be provided on the various adapters of the accessing system for the same purpose.

The proximal shaft section 33 of the guide member 31 is shown extending out of the port 24 in the adapter 17 on the proximal end of the first proximal extension 16 of the tubular support member 10. The proximal shaft section 52 of stabilizing member 50 extends out the port 27 in adapter 20 on second proximal extension 18. A stabilizer holder 63 is clamped on one end to the introducer 60 extending out of the patient 61 and the other end of the holder 63 is provided with a clamp 64 having arms 65 and 66 which clamp onto the proximal shaft section 52 of the stabilizer member 50, as shown in more detail in FIG. 10. As shown in FIG. 10, clamp 64 has a threaded wing nut 67 is utilized to close the arms 65 and 66 so as to firmly hold the proximal shaft section 52 of the stabilizing member 50.

In FIG. 11 illustrates the distal portion of the assembly shown in FIG. 9 operatively disposed within the patients right heart. The distal portion of the tubular member 10 is disposed within the patient's right atrium 68. The stabilizer member 50 is shown extending out of the port 28 of tubular support member 10, through the patient's mitral valve 69 into the right ventricle 70 with a curved distal shaft section 53 in a J-shape being disposed within the apex 71 of the right ventricle 70. The distal shaft section 44 of guide member 31 extends out of the port 25 of the distal tip 14 of tubular support member 10 with its distal section seated in the coronary sinus ostium 72 thereby providing access to the coronary sinus.

A distal portion of a pacing lead 73 is shown in FIG. 11 disposed within the patient's cardiac vein 75 disposed on the left side 76 of the patient's heart adjacent to the patient's left ventricle (not shown). The pacing lead 73 is generally too large to be introduced into the accessing system, so as a result, a guidewire may be introduced through the guide member 31 when its distal end is disposed within the coronary sinus ostium. The accessing system may then be removed leaving the guidewire in place. A guiding catheter having a larger inner lumen may then be advanced over the guidewire left in place to provide a more distal access within the coronary ostium. A first guidewire may then be removed and a second guidewire having greater steerability may then be advanced through the larger guiding catheter to the desired location within the patient's cardiac vein 75. The pacing lead 73 may then be advanced over the second guidewire to the desired location within the vein 75 as shown in FIG. 11. The pacing lead 73 is provided with an electrode 77 on its distal end which is utilized to pace the left ventricle. Additionally, other pacing leads may also be used to pace other portions of the patient's heart. In this manner the hearts of patient's with CHF can be effectively controlled with the one or more pacing leads to improve blood output from the left and right ventricles.

While FIG. 11 illustrates a pacing lead 73 delivered through the patient's coronary sinus 74 and blood vessels which drain into the coronary sinus, those skilled in the art will recognize that once coronary access is made a wide variety of other therapeutic and diagnostic devices may then be delivered to the coronary sinus and the blood vessels which drain to the coronary sinus. For example, a wide variety of electrophysiology and drug delivery catheters may be delivered.

Figure 12:
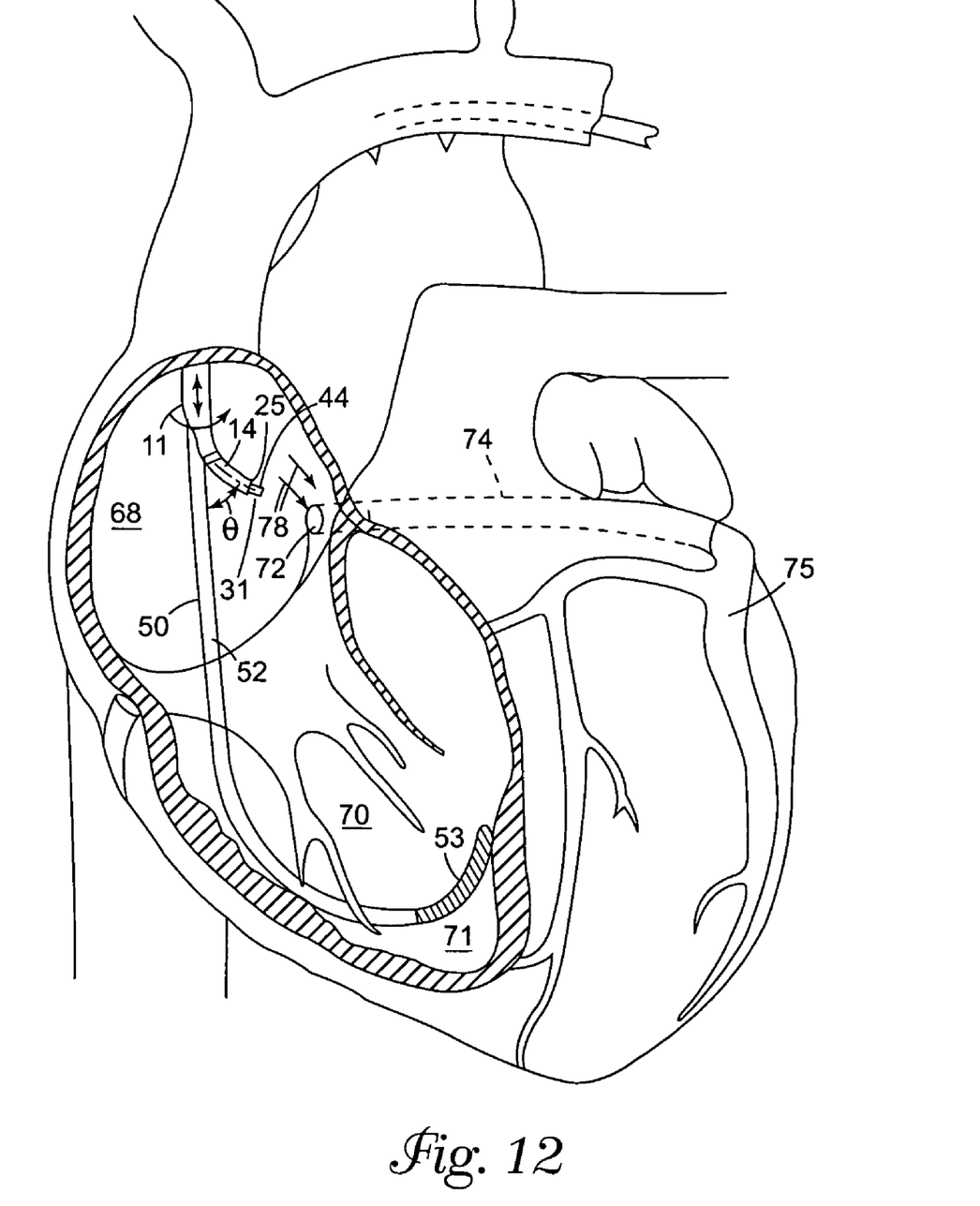
FIG. 12 is a schematic elevational view illustrating a systematic method of accessing the opening for the patient's coronary sinus.

FIG. 11 illustrates the installed system in a heart having a normal shape. As mentioned above, the hearts of CHF patients can be enlarged and deformed which makes accessing the patient's coronary ostium difficult and time consuming for the physician. FIG. 12 illustrates systematic steps for guiding the distal end of the guiding member 31 into the ostium 72 of the patient's coronary sinus particularly when the heart chamber is deformed or enlarged. The assembly is disposed in the right atrium 68 of the patient with the distal portion 53 of the stabilizer 50 disposed in the apex 71 of the right ventricle 70. The tubular support member 10 is rotated about the stabilizer 50 with the distal section 44 of the guiding member 31 extending out the distal port 25 toward the wall of the right atrium 68. In this manner the distal section 44 can sweep against a wide region of the atrial wall as shown by the arrows 78 in a sequential pattern to ensure rapid accession of the coronary ostium 72. After each sweep, the tubular support member 10 can be moved along (up or down) the shaft of the stabilizing member 50 so that a region of the atrial wall can be systematically explored. The electrode 43 (shown on FIG. 5) on the distal end of the guiding member 31 can be employed by comparing its EKG output with that of a standard electrode to allow the physician to determine its position within the atrial chamber. Different locations within the right atrium provide different signal characteristics which the physician can use to determine the electrode's location.

Figure 13:
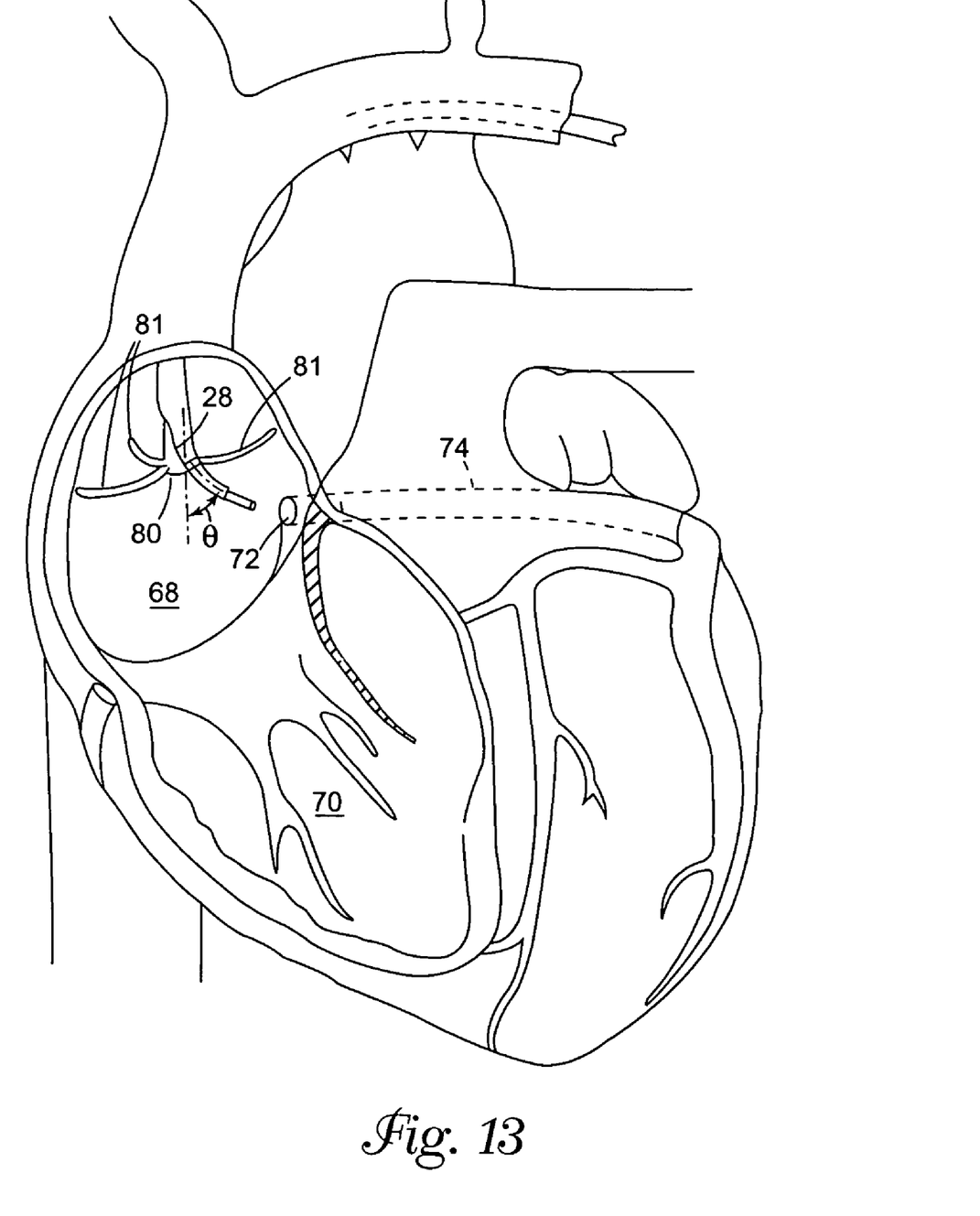
FIG. 13 is a schematic elevational view of a second alternative wherein a stabilizing member in the form of a plurality of arms which extend outwardly when the member extends out of the distal end of the tubular support member to engage the atrial wall.

FIG. 13 illustrates an alternative stabilizer member 80 which extends through the second inner lumen 26 (shown in FIG. 2) of the tubular support member 10 and which has a plurality of arms 81 (three are shown) which extend outwardly to engage the wall of the right atrium 68 when the stabilizer 80 extends out of the port 28 of the tubular support member 10. The arms 81 are preferably formed of materials such as superelastic NiTi alloy which is in a temperature stable austenite phase at body temperature but which exhibits stress induced martensite formation.

The shafts of the tubular support member 10 and the guide member 31 may be formed of conventional polymeric material, including polyethylene, nylons, polyether block amides available under the trade name Pebax from Elf Atochem and polyurethanes used for intravascular catheters. The inner lumens of these members may be formed by tubular members formed from a lubricious material such as high density polyethylene and fluoropolymers (e.g. Teflon®). The adapters may be formed in a conventional manner from suitable polycarbonate materials.

The tubular support member 10 and the guide member 31 may be provided with a braided support structure within the walls thereof formed of metallic materials (e.g. stainless steel) or high strength polymeric materials such as Kevlar®, polyimide and polyetheretherketone (PEEK).

For approaches through the superior vena cava, the length of the tubular support member 31 is generally about 35 cm to about 55 cm, with a nominal length preferably about 45 cm. The ID of the first inner lumen 24 is about 0.023 to about 0.035 inch (0.58–0.89 mm) and the ID of the second inner lumen 26 is about 0.026 inch (0.66 mm) to about 0.036 inch (0.9 mm). The guide member 31 is generally about 5 to about 15 cm longer than the tubular support member 10 and has an OD less than the ID of the first inner lumen 24 and typically about 0.23 to about 0.03 inch (0.58–0.76 mm), typically about 0.017 inch (0.43 mm). The ID of the inner lumen 35 within the guide member 30 is about 0.015 inch (0.38 mm) to about 0.02 inch (0.5 mm), with a nominal of about 0.027 inch (0.69 mm). Over the wire versions and rapid exchange versions of the tubular support member 10 may be utilized. With the over-the-wire version the second lumen 26 extends within the shaft of the tubular support member 10 to its proximal end; whereas, with a rapid exchange version the second lumen is quite short and extends only through the distal portion of the tubular support member.

While not shown in the drawings, the tubular support member may be delivered to the right atrium through a guiding catheter. Moreover, it will be apparent from the foregoing that, while particular forms of the invention have been illustrated and described, various modifications can be made without departing from the spirit and scope of the invention. Those skilled in the art will also recognize that features shown in one embodiment may be utilized in other embodiments.

As used herein the terms "member", "elements" and words of similar import with reference to for performing some function or step shall not invoke the provisions of 35 U.S.C. §112 (par. 6) unless claims directed thereto use the term "means" or "step" followed by a specific function or method.

What is claimed is:

1. A coronary sinus accessing system, comprising:
   a. an elongated tubular support member configured for intravascular advancement to a right atrium, comprising:
      an elongated shaft which has proximal and distal shaft sections and a first lumen extending within the proximal and distal shaft sections; and
      a distal tip which has an opening providing exterior access to, and in fluid communication with, the first lumen in the elongated shaft and which is oriented at an angle with respect to a longitudinal axis of the shaft;
   b. a guide member which has proximal and distal shaft sections, which is disposed within the first lumen of the tubular support member, which is configured for longitudinal movement through the first lumen and out the distal tip opening and which has a distal extremity configured for entry into a coronary sinus ostium; and
   c. a stabilizing member deployable outside the tubular support member through an opening at the distal section of the elongated shaft and configured to maintain alignment of the tubular support member within the right atrium, the tubular support member configured to rotate about a longitudinal axis of the stabilizing member when the stabilizing member is deployed outside the tubular support member.

2. The accessing system of the claim 1 wherein the tubular support member has a second lumen extending therein.

3. The accessing system of claim 2 wherein the stabilizing member has an elongated core and a flexible body disposed about a distal portion of the core and is configured to be slidably advanced through the second lumen extending within the tubular support member.

4. The accessing system of claim 3 wherein the stabilizer member has a distal section which is configured to be seated within an apex of a right ventricle.

5. The accessing system of claim 4 wherein the distal section of the stabilizer member has a J-shape.

6. The accessing system of claim 3 wherein the stabilizer member has a plurality of indicia on the core thereof to measure axial movement of the tubular support member.

7. The accessing system of claim 2 wherein the distal shaft section of the tubular support member is provided with an electrode.

8. The accessing system of claim 1 wherein the guide member has an inner lumen extending therein.

9. The accessing system of claim 1 wherein the guide member has an electrode on the distal shaft section thereof.

10. The accessing system of claim 9 wherein the proximal shaft section of the guide member has a second proximal extension with an electrical connector thereof electrically connected to the electrode on the distal shaft section thereof.

11. The accessing system of claim 10 wherein the electrical connector is electrically connected to the electrode on the distal shaft section by means of a conductor.

12. The accessing system of claim 1 wherein the distal tip of the tubular support member is oriented at an angle of about 20° to about 70° with respect to a longitudinal axis of the shaft.

13. The accessing system of claim 1 wherein the distal tip of the tubular support member is oriented at an angle of about 30° to about 60°.

14. A tubular support member configured for intravascular advancement through a patient's vasculature to a right atrium thereof, comprising:
  a. an elongated shaft which has proximal and distal shaft sections, a longitudinal axis and at least first and second lumens extending through the proximal and distal shaft sections;
  b. a distal tip on the distal shaft section oriented at an angle with respect to the longitudinal axis of the shaft, the distal tip having a first opening providing external access to, and in fluid communication with, the first lumen and configured to facilitate advancement of a guide member through the first opening; and
  c. a second opening in the distal shaft section providing external access to, and in fluid communication with, the second lumen in the elongated shaft and configured to facilitate advancement of a stabilizing member through the second opening and into the right atrium, a longitudinal axis of the second lumen aligned relative to the second opening to facilitate rotation of the tubular support member about a longitudinal axis of the stabilizing member when the stabilizing member is deployed beyond the second opening.

15. The member of claim 14 wherein the distal tip of the tubular support member is oriented at an angle of about 20° to about 70° with respect to a longitudinal axis of the shaft.

16. The member of claim 14 wherein the distal tip of the tubular support member is oriented at an angle of about 30° to about 60°.

17. A method for accessing a coronary sinus comprising:
  a. providing an accessing system, comprising;
    an elongated tubular support member configured for intravascular advancement to a right atrium, comprising:
      an elongated shaft which has proximal and distal shaft sections and a first lumen extending within the proximal and distal shaft sections; and
      a distal tip which has an opening providing exterior access to, and in fluid communication with, the first lumen in the elongated shaft and which is oriented at an angle with respect to a longitudinal axis of the shaft;
    a guide member which has proximal and distal shaft sections, which is disposed within the first lumen of the tubular support member, which is configured for longitudinal movement through the first lumen and out the distal tip opening and which has a distal extremity configured for entry into a coronary sinus ostium; and
    a stabilizing member deployable outside the tubular support member at the distal section of the elongated shaft and configured to maintain alignment of the tubular support member within the right atrium;
  b. percutaneously introducing the components of the system into a venous system and advancing the system components within the venous system until the distal extremity of the tubular support member is disposed and stabilized within the right atrium; and
  c. extending the guide member out of the opening in the distal tip of the tubular support member until the distal end of the guide member enters the coronary sinus ostium.

18. A method of treating a heart, comprising:
  a. providing a coronary accessing system, comprising;
    an elongated tubular support member configured for intravascular advancement to a right atrium, comprising:
      an elongated shaft which has proximal and distal shaft sections and a first lumen extending within the proximal and distal shaft sections; and
      a distal tip which has an opening providing exterior access to, and in fluid communication with, the first lumen in the elongated shaft and which is oriented at an angle with respect to a longitudinal axis of the shaft;
    a guide member which has proximal and distal shaft sections, which is disposed within the first lumen of the tubular support member, which is configured for longitudinal movement through the first lumen and out the distal tip opening and which has a distal extremity configured for entry into a coronary sinus ostium; and
    a stabilizing member deployable outside the tubular support member at the distal section of the elongated shaft and configured to maintain alignment of the tubular support member within the right atrium;
  b. introducing the components of the coronary accessing system into a venous system and advancing the system components within the venous system until the distal extremity of the tubular support member is disposed and stabilized within the right atrium;
  c. extending the guide member out of the opening in the distal tip of the tubular support member until the distal end of the guide member enters the coronary sinus ostium; and
  d. advancing an elongated intravascular device through or over the guide member, into a coronary sinus.

19. A coronary sinus accessing system, comprising:
  a. a tubular support means configured for intravascular advancement to a right atrium, comprising:
    an elongated shaft which has proximal and distal shaft sections, a longitudinal axis and a first lumen extending within the proximal and distal shaft sections; and
    a distal tip which has an opening providing external access to, and in fluid communication with, the first lumen in the elongated shaft and which is oriented at an angle with respect to the longitudinal axis of the shaft;

b. a guide means which is slidably disposed within the first lumen of the tubular support means, which is configured for longitudinal movement through the first lumen and out the distal tip opening and which has a distal extremity configured for entry into a coronary sinus ostium and a delivery therein of a therapeutic or diagnostic device; and c. a stabilizing means deployable outside the tubular support means through an opening at the distal section of the elongated shaft and configured to maintain the alignment of the tubular support means within the right atrium, the tubular support means configured to rotate about a longitudinal axis of the stabilizing means when the stabilizing means is deployed outside the tubular support means.

20. A coronary sinus accessing system, comprising:

an elongated tubular support member configured for intravascular advancement to a right atrium, the elongated tubular support member comprising an elongated shaft having proximal and distal shaft sections and a first lumen extending within the proximal and distal shaft sections, the elongated tubular support member further comprising a distal tip having a first opening providing exterior access to, and in fluid communication with, the first lumen, and a second opening in the distal shaft section providing external access to, and in fluid communication with, a second lumen in the elongated shaft, the distal tip oriented at an angle with respect to a longitudinal axis of the shaft;

means, deployable through the first lumen and the first opening, for entering a coronary sinus ostium; and means, deployable outside the tubular support member via the second lumen and the second opening, for stabilizing the tubular support member within the right atrium, the tubular support member rotatable about a longitudinal axis of the stabilizing means when the stabilizing means is deployed outside the tubular support member.

21. The accessing system of claim 1 wherein the tubular support member is rotatable about the longitudinal axis of the stabilizing member through a sweep angle greater than or equal to 360°.

22. The accessing system of claim 1 wherein the tubular support member is rotatable about the longitudinal axis of the stabilizing member through a sweep angle no greater than 360°.

23. The accessing system of claim 1 wherein the stabilizing member comprises two or more stabilizing arms each configured to contact a heart chamber wall.

24. The accessing system of claim 23 wherein the heart chamber wall comprises a wall of the right atrium.

25. The accessing system of claim 23 wherein the tubular support member is rotatable about the longitudinal axis of the stabilizing member through a sweep angle limited by an angle defined between adjacent ones of the two or more stabilizing arms.

26. The member of claim 14 wherein the elongated shaft is rotatable about the longitudinal axis of the stabilizing member through a sweep angle no greater than 360°.

27. The member of claim 14 wherein the elongated shaft is rotatable about the longitudinal axis of the stabilizing member through a sweep angle limited by the stabilizing member.

28. The method of claim 17 comprising:

extending the stabilizing member beyond a distal end of the tubular support member; and contacting a heart chamber wall using the stabilizing member.

29. The method of claim 28 wherein contacting the heart chamber wall comprises contacting the heart chamber wall at a plurality of spaced-apart locations.

30. The method of claim 28 wherein the heart chamber wall comprises a wall of the right atrium.

31. The method of claim 28 wherein the heart chamber wall comprises a wall of the right ventricle.

32. The method of claim 28 comprising rotating the tubular support member relative to the longitudinal axis of the stabilizing member through a sweep angle such that the guide member sweeps through an angle equal to the sweep angle.

33. The method of claim 32 wherein the sweep angle is greater than or equal to 360°.

34. The method of claim 32 wherein the sweep angle is no greater than 360°.

35. The method of claim 18 comprising:

extending the stabilizing member beyond a distal end of the tubular support member; and contacting a heart chamber wall using the stabilizing member.

36. The method of claim 28 wherein contacting the heart chamber wall comprises contacting the heart chamber wall at a plurality of spaced-apart locations.

37. The method of claim 28 wherein the heart chamber wall comprises a wall of the right atrium.

38. The method of claim 28 wherein the heart chamber wall comprises a wall of the right ventricle.

39. The method of claim 28 comprising rotating the tubular support member relative to the longitudinal axis of the stabilizing member through a sweep angle such that the guide member sweeps through an angle equal to the sweep angle.

40. The method of claim 39 wherein the sweep angle is greater than or equal to 360°.

41. The method of claim 39 wherein the sweep angle is no greater than 360°.

42. The system of claim 20 wherein the stabilizing means comprises engaging means for engaging a wall of the right atrium at a plurality of space-apart locations.

43. The system of claim 20 wherein the stabilizing means comprises engaging means for engaging a portion of the right ventricle.

44. The system of claim 20 wherein the tubular support member is rotatable about the longitudinal axis of the stabilizing means through a sweep angle greater than or equal to 360°.

45. The system of claim 20 wherein the tubular support member is rotatable about the longitudinal axis of the stabilizing means through a sweep angle no greater than 360°.

* * * * *